US006489525B1

(12) United States Patent
Erdman et al.

(10) Patent No.: US 6,489,525 B1
(45) Date of Patent: Dec. 3, 2002

(54) METHODS FOR PREPARING PRIMARY ALKYL BROMIDES

(75) Inventors: David T. Erdman, Liberty, MO (US); Jonathan D. Spicher, Parkville, MO (US); Mary F. Lamar, Overland Park, KS (US); David E. Cockrill, Kansas City, MO (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/972,583

(22) Filed: Oct. 5, 2001

(51) Int. Cl.[7] ................................................ C07C 17/20
(52) U.S. Cl. ..................................................... 570/260
(58) Field of Search .............................. 570/260, 261, 570/262

(56) References Cited

U.S. PATENT DOCUMENTS

| 2,244,629 A | | 6/1941 | Livak et al. | |
|---|---|---|---|---|
| 2,359,828 A | | 10/1944 | Davies | |
| 3,923,914 A | * | 12/1975 | Kobetz et al. | ............... 570/260 |
| 3,992,432 A | | 11/1976 | Napier et al. | |
| 4,144,265 A | | 3/1979 | Dowd et al. | |
| 4,334,103 A | | 6/1982 | Töke et al. | |
| 4,424,385 A | | 1/1984 | Markofsky | |
| 4,978,769 A | | 12/1990 | Kysela et al. | |
| 4,978,795 A | | 12/1990 | Newallis et al. | |
| 5,118,842 A | | 6/1992 | Newallis et al. | |

OTHER PUBLICATIONS

J. Chem. Soc., (month unavailable) 1955, pp. 3173–3177, E.D. Hughes, C.K. Ingold and J.D.H. Mackie, Mechanism of Substitutjion at a Saturated Carbon Atom. Part XLIII. Kinetic of the Interaction of Chloride Ions with Simple Alkyl Bromides in Acetone.

Starks and Liotta, Phase Transfer Catalysis, Academic Press, New York (month unavailable) 1978, pp. 112–125, III. Halide Displacement Reactions.

W.P. Weber and G.W. Gokel, Phase Transfer Catalysis in Organic Synthesis, Springer–Verlag Berlin Heidelberg New York (month unavailable) 1977, Reactions of Other Nucleophiles, pp. 117–124.

* cited by examiner

*Primary Examiner*—Alan Siegel
(74) *Attorney, Agent, or Firm*—Joseph C. Gil; John E. Mrozinski, Jr.

(57) ABSTRACT

Methods of converting methyl chloride to methyl bromide include the steps of providing a composition comprising a bromide salt and water; contacting the composition with a primary alkyl chloride; and recovering methyl bromide.

14 Claims, No Drawings

METHODS FOR PREPARING PRIMARY ALKYL BROMIDES

FIELD OF THE INVENTION

This invention relates to methods of preparing primary alkyl bromides, particularly methyl bromide. The invention also relates to methods of converting methyl chloride to methyl bromide and to methods of reducing the level of bromide salt in aqueous compositions.

BACKGROUND OF THE INVENTION

Primary alkyl bromides, such as methyl bromide, may be used as fumigants, alkylating agents, or intermediates in the synthesis of other chemical compounds, in particular pharmaceutical or agricultural chemicals.

Methyl bromide may be prepared by treating methanol with hydrobromic acid and sulfuric acid. Unfortunately, such processes required the handling and/or disposing noxious and/or dangerous compounds.

Salt exchange reactions include reactions wherein an alkyl halide is converted to another alkyl halide, such as, for example, the Finkelstein reaction wherein alkyl chlorides or bromides are converted to alkyl iodides using solid potassium or sodium iodide in acetone. Unfortunately, such reactions require the handling or large volumes of acetone, and the equilibrium constants for alkyl chloride/alkyl bromide exchanges in acetone often favor the alkyl chloride.

Hughes et al., *J. Chem. Soc.*, 3173–3175 (1955), teach that the displacement of bromine from alkyl bromides using lithium chloride in dry acetone is only mildly reversible. Starks and Liotta, *Phase Transfer Catalysis*", Academic Press, New York, New York (1978), teach the use of phase transfer catalysts in halide exchange reactions in two-phase systems and in homogenous organic reactions, and disclose that the displacement of chloride ion on octyl bromide is faster than bromide ion displacement on octyl chloride.

Handling large volumes of acids may be difficult and/or costly. Additionally, processes using large amounts of sulfuric acid may generate an aqueous waste stream comprising $NaSO_4$ as well as residual sulfuric acid, and $NaSO_4$ generally causes more environmental problems than sodium salts such as NaCl or NaBr. Thus, there is a need for facile methods of producing primary alkyl bromides which do not require the use of large volumes of acids.

As handling large volumes of some organic solvents may be difficult and/or costly, there is a need for methods of producing primary alkyl bromides which do not require the use of large volumes of solvents such as acetone.

There is also a need for methods of reducing the level of bromide salts in aqueous compositions.

There is a need for methods of regenerating alkyl bromides from bromide salts which are formed when alkyl bromides, such as methyl bromide, are used as reactants.

SUMMARY OF THE INVENTION

Accordingly, it is an object of the present invention to obviate problems of the prior art.

It is a further object of the present invention to provide methods of preparing alkyl bromides.

It is also an object of the present invention to provide methods of preparing alkyl bromides which do not require the handling, storage or disposal of large volumes of acetone, hydrobromic acid or sulfuric acid.

It is another object of the present invention to provide methods of removing bromide salts from liquid compositions.

It is a further object of the present invention to provide methods of regenerating alkyl bromides from bromide salts.

These and additional objects are provided by the methods of the invention.

In one embodiment the invention is directed to methods of converting methyl chloride to methyl bromide comprising:
(a) providing a composition comprising a bromide salt and water;
(b) contacting the composition with methyl chloride; and
(c) recovering a gaseous product comprising methyl bromide.

In another embodiment, the invention is directed to methods of preparing a primary alkyl bromide comprising:
(a) providing a composition comprising a bromide salt and water;
(b) contacting the composition with a primary alkyl chloride thereby forming a primary alkyl bromide; and
(c) recovering the primary alkyl bromide.

In a further embodiment, the invention is directed to methods of reducing the level of bromide salt in an aqueous composition comprising:
(a) providing an aqueous composition comprising bromide salt and water;
(b) reacting at least a portion of the bromide salt with a primary alkyl chloride to form a primary alkyl bromide; and
(c) recovering the primary alkyl bromide from the aqueous composition.

In yet another embodiment, the invention is directed to methods of converting methyl chloride to methyl bromide comprising:
a) providing a reaction column oriented substantially vertically along its axis and having an upper portion and a lower portion, wherein the reaction column contains packing suitable for continuous extractions;
(b) introducing an aqueous feed into the upper portion of the reaction column, wherein the aqueous feed comprises water and a bromide salt selected from the group consisting of the alkali metal bromides, alkaline earth metal bromides and combinations thereof;
(c) introducing methyl chloride gas into the lower portion of the reaction column; and
(d) allowing at least one portion of the aqueous feed and at least a portion of the methyl chloride to contact each other within the reaction column thereby converting at least a portion of the methyl chloride to methyl bromide.

These and additional aspects, objects and advantages of the invention are more fully described in the following detailed description.

DETAILED DESCRIPTION

The present invention is directed to the preparation of primary alkyl bromides in the presence of a liquid. The present invention is also directed to methods of reducing the level of bromide salts in an aqueous solution, and methods of regenerating alkyl bromides.

The primary alkyl bromides are prepared by providing a composition comprising bromide salt and a liquid, preferably water; contacting the composition with a primary alkyl chloride thereby forming a primary alkyl bromide; and recovering the primary alkyl bromide. In one embodiment the primary alkyl chloride is gaseous methyl chloride and/or methyl chloride dissolved in liquid. Methods in accordance with the invention may be used to regenerate alkyl bromides from bromide salts which are formed when alkyl bromides are used as reactants.

Methods in accordance with the invention avoid the use of large volumes of acids and/or organic solvents such as acetone. Thus any resulting aqueous waste stream may be easily handled and/or treated.

While not being bound by theory, it is believed that the reaction proceeds as set forth below:

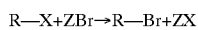

wherein R is a primary alkyl, preferably a $C_1$–$C_{20}$ primary alkyl, more preferably a $C_1$–$C_5$ alkyl; even more preferably a $C_1$–$C_2$ alkyl; X is a halogen, preferably a halogen other than Br, more preferably Cl; Z is a cation such hydrogen, sodium, potassium, lithium, magnesium, calcium or copper, preferably hydrogen, sodium, potassium or lithium.

Suitable bromide salts include hydrogen bromide, alkali metal bromides, alkaline earth metal bromides, organic quaternary bromides and combinations thereof, preferably the bromide salts are selected from the group consisting of alkali metal bromides, alkaline earth metal bromides and combinations thereof. In one embodiment the bromide salt is selected from the group consisting of sodium bromide, potassium bromide, lithium bromide, hydrogen bromide and combinations thereof. In another embodiment the bromide salt is an organic quaternary bromide, such as tetramethyl ammonium bromide or tetraethyl ammonium bromide.

The bromide salt may be present in a mixture with salts other than bromide salts, such as sodium sulfate and sodium chloride. The bromide salt may be present in the aqueous composition at a concentration of from about 1% to about 50%, preferably from about 5% to about 35%, by weight. The aqueous composition may further comprise water-miscible organic solvents.

The preparation of the primary alkyl bromide may occur in the substantial absence of water-immiscible organic solvent. As used herein "substantial absence of water-immiscible organic solvent" is intended to mean to liquid comprises less than 10%, by weight, water-immiscible organic solvent. Water-immiscible organic solvents include $C_5$–$C_{20}$ aliphatic and cycloaliphatic hydrocarbon solvents, mono- and polycyclic solvents, di($C_1$–$C_4$ alkyl)formamides, ketones such as $C_4$–$C_8$ ketones, and combinations thereof. In one embodiment the aqueous composition is free of water-immiscible organic solvents. In one embodiment the preparation of the primary alkyl bromide occurs in the substantial absence, preferably the absence, of acetone.

As used here, "primary alkyl chloride" is intended to refer to compounds having a chloride on a terminal alkyl carbon, and is intended to include arylalkyls having a chloride on a terminal alkyl carbon. The primary alkyl chloride molecules generally have from about 1 to about 20, preferably from about 1 to about 5, more preferably from about 1 to about 2, carbon atoms. Suitable primary alkyl chlorides include 1-chloroethane, methyl chloride, and combinations thereof. Preferably the primary alkyl chloride is methyl chloride.

The bromide salt is present in an amount to provide a molar equivalent ratio of bromide ions to primary alkyl chloride of from about 1:10 to about 10:1. In one preferred embodiment the primary alkyl chloride is methyl chloride, and the bromide salt is present in an amount to provide a molar equivalent ratio of bromide ions to methyl chloride of from about 1:10 to about 10:1.

In one embodiment of the invention the step of contacting the composition comprising the bromide salt and water with the primary alkyl chloride, preferably methyl chloride, occurs in the substantial absence of phase transfer catalyst. Phase transfer catalysts include organic quaternary Group V salts, crown ethers, cryptanes, polyalkylene glycols such as poly($C_2$–$C_4$ alkylene glycols), tris[2-(2-methoxyethoxy)-ethyl]amine (TDA-1), amines or phosphines which are quaternized under the reaction conditions, and combinations thereof. As used herein "substantial absence of phase transfer catalyst" is intended to mean that the reaction mixture comprising the bromide salt, water and primary alkyl chloride comprises or no more than about 0.5%, preferably less than about 0.5%, by weight phase transfer catalyst. In one embodiment the reaction mixture is free of phase transfer catalyst.

The methods in accordance with the present invention may be performed at any pressure and temperature sufficient for the desired reaction to occur. Generally the methods are performed at a temperature of from about 40° C. to about 200° C., preferably from about 60° C. to about 80° C., and at pressure of from about 0 to about 20 atmospheres.

The conversion of the primary alkyl chloride to primary alkyl bromide may be performed batchwise, semi-batchwise or continuously, and gases produced during the conversion may be purified by continuous or batchwise distillation, or by pressure swing absorption methods.

Any suitable reactor may be used, including fixed-bed reactors. For example, one embodiment of the invention comprises:

(a) providing a reaction column oriented substantially vertically along its axis and having an upper portion and a lower portion, wherein the reaction column contains packing suitable for continuous extractions;

(b) introducing an aqueous feed into the upper portion of the reaction column, wherein the aqueous feed comprises water and a bromide salt selected from the group consisting of the alkali metal bromides, alkaline earth metal bromides and combinations thereof;

(c) introducing methyl chloride gas into the lower portion of the reaction column; and (d) allowing at least one portion of the aqueous feed and at least a portion of the methyl chloride to contact each other within the reaction column thereby converting at least a portion of the methyl chloride to methyl bromide.

Methods in accordance with the present invention provide good recoveries of the bromide salt. Generally at least about 30%, preferably at least about 50%, more preferably at least about 60%, by weight, of the bromide salt is converted to primary alkyl bromide. In one embodiment, the primary alkyl bromide is methyl bromide, and at least about 30%, preferably at least about 50%, more preferably at least about 60%, even more preferably at least about 80%, of the bromide salt is converted to methyl bromide. In one embodiment of the invention any unreacted primary alkyl chloride is recovered and may be used recycled in a subsequent bromide salt conversion.

Excessive hydrolysis of the primary alkyl bromide product can be avoided using methods of the present invention. Generally no more than about 25%, preferably no more than about 10%, more preferably no more than about 5%, by weight, of the primary alkyl bromide undergoes hydrolysis.

In one embodiment of the invention the step of contacting a composition comprising the bromide salt and water with the primary alkyl chloride, preferably methyl chloride, occurs in the substantial absence of phase transfer catalyst, while in another embodiment of the invention the step of contacting a composition comprising the bromide salt and water with the primary alkyl chloride, preferably methyl chloride, occurs in the substantial absence of phase transfer catalyst and water-immiscible organic solvent. In one embodiment of the invention the step of contacting a composition comprising the bromide salt and water with the primary alkyl chloride, preferably methyl chloride, occurs in the substantial absence of phase transfer catalyst and the substantial absence of water-immiscible solvent.

In one embodiment the primary alkyl chloride is gaseous methyl chloride and/or methyl chloride dissolved in a water-immiscible solvent, while in another embodiment the primary alkyl chloride is gaseous methyl chloride. The bromide salt may be selected from the group consisting of alkali metal bromides, alkaline earth metal bromides and combinations thereof.

Methods in accordance with the present invention may be used to reduce the level of bromide salt in aqueous compositions. Accordingly, the method may comprise converting at least a portion of a bromide salt in an aqueous composition to primary alkyl bromides, and removing the primery alkyl bromides from the aqueous composition. The primary alkyl chloride may be selected from the group consisting of 1-chloroethane, methyl chloride, and combinations thereof, preferably the primary alkyl chloride is methyl chloride. The bromide salt may be selected from the group consisting of alkali metal bromides, alkaline earth metal bromides, organic quaternary bromides and combinations thereof, preferably selected from the group consisting of alkali metal bromides, alkaline earth metal bromides and combinations thereof.

The bromide salt may be present in the aqueous composition at a level of from about 1% to about 50%, by weight of the composition, preferably at a level of from about 5% to 35%, by weight of the composition. The process may be performed at a temperature of at least about 40° C., preferably from about 40° C. to about 200° C., more preferably from about 50° C. to about 90° C., and at a pressure of from about 0 to about 20 atmospheres.

Generally at least about 30%, preferably at least about 50%, more preferably at least about 60%, by weight, of the bromide salt is removed from the aqueous compositions.

Throughout the examples and the present specification, parts and 20 percentages are by weight unless otherwise specified. The following example is illustrative only and is not intended to limit the scope of the methods of the invention as defined by the claims.

EXAMPLES

Example 1

About 500 g of water and about 200 g of sodium bromide are placed in a reactor and heated to about 86° C. The reactor is then pressurized to about 64 psi with methyl chloride (about 0.8 moles). After 60 minutes the gas phase is analyzed. The conversion is about 36%.

Example 2

About 500 g of water and about 231 g of sodium bromide are placed in a reactor and heated to about 71° C. Methyl chloride is added to a pressure of about 55 psi (about 0.9 moles). After 60 minutes the gas phase is analyzed. The conversion is about 30%.

Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

What is claimed is:

1. A method of converting methyl chloride to methyl bromide comprising:
   reacting a composition comprising a bromide salt and water with gaseous methyl chloride; and
   recovering a product comprising methyl bromide,
   wherein said composition is substantially or completely free of phase transfer catalyst and water-immiscible organic solvent.

2. The method of claim 1, wherein the bromide salt is selected from the group consisting of alkali metal bromides, alkaline earth metal bromides, organic quaternary bromides and combinations thereof.

3. The method of claim 1, wherein the bromide salt is selected from the group consisting of alkali metal bromides, alkaline earth metal bromides and combinations thereof.

4. The method of claim 1, wherein the composition comprises an amount of bromide salt sufficient to provide a molar equivalent ratio of bromide ion to methyl chloride of at least about 1:1.

5. A method of preparing a primary alkyl bromide comprising:
   reacting a composition comprising a bromide salt and water with a gaseous primary alkyl chloride thereby forming a primary alkyl bromide; and
   recovering the primary alkyl bromide,
   wherein said composition is substantially or completely free of phase transfer catalyst and water-immiscible organic solvent.

6. The method of claim 5, wherein the primary alkyl chloride is selected from the group consisting of 1-chlorobutane, 1-chloroethane, methyl chloride, benzyl chloride, and combinations thereof.

7. The method of claim 5, wherein the bromide salt is selected from the group consisting of alkali metal bromides, alkaline earth metal bromides and combinations thereof.

8. The method claim 5, wherein the step of reacting the composition with a primary alkyl chloride o curs at a temperature of at least about 40° C.

9. A method of reducing the level of bromide salt in an aqueous composition comprising:
   reacting in an aqueous composition comprising bromide salt and water at least a portion of the bromide salt with a gaseous primary alkyl chloride to form a primary alkyl bromide; and
   recovering the primary alkyl bromide from the aqueous composition,
   wherein said composition is substantially or completely free of phase transfer catalyst and water-immiscible organic solvent.

10. The method of claim 9, wherein the primary alkyl chloride is selected from the group consisting of 1-chlorobutane, 1-chloroethane, methyl chloride, benzyl chloride, and combinations thereof.

11. The method of claim 9, wherein the bromide salt is selected from the group consisting of alkali metal bromides, alkaline earth metal bromides, organic quaternary bromides and combinations thereof.

12. The method of claim 9, wherein the bromide salt is selected from the group consisting of alkali metal bromides, alkaline earth metal bromides and combinations thereof.

13. The method of claim 9, wherein the step of reacting at least a portion of the bromide salt with a primary alkyl chloride occurs at a temperature of at least about 40° C.

14. A method of converting methyl chloride to methyl bromide comprising:

introducing an aqueous feed comprising water and a bromide salt selected from the group consisting of the alkali metal bromides, alkaline earth metal bromides and combinations thereof into the upper portion of a reaction column oriented substantially vertically along its axis and having an upper portion and a lower portion, wherein the reaction column contains packing suitable for continuous extractions;

introducing methyl chloride gas into the lower portion of the reaction column: and reacting at least a portion of the aqueous feed with at least a portion of the methyl chloride within the reaction column thereby converting at least a portion of the methyl chloride to methyl bromide, wherein said aqueous fee is substantially or completely free of phase transfer catalyst and water-immiscible organic solvent.

* * * * *